(12) United States Patent
Nan

(10) Patent No.: US 7,572,220 B2
(45) Date of Patent: Aug. 11, 2009

(54) COLLAPSIBLE VACUUM DEVICE

(75) Inventor: Simon Siu Man Nan, Ontario (CA)

(73) Assignee: Nanma Manufacturing Co., Ltd., Hong Kong (HK)

( * ) Notice: Subject to any disclaimer, the term of this patent is extended or adjusted under 35 U.S.C. 154(b) by 842 days.

(21) Appl. No.: 11/109,430

(22) Filed: Apr. 19, 2005

(65) Prior Publication Data

US 2006/0235266 A1    Oct. 19, 2006

(51) Int. Cl.
*A61F 5/00*    (2006.01)
(52) U.S. Cl. ...................................................... 600/38
(58) Field of Classification Search ............ 600/38–41; 128/844, 912, 918
See application file for complete search history.

(56) References Cited

U.S. PATENT DOCUMENTS

| 734,238 A | 7/1903 | Ottignon |
| 4,378,008 A | 3/1983 | Osbon, Sr. |
| 4,718,411 A | 1/1988 | Stewart |
| 5,020,522 A | 6/1991 | Stewart |
| 5,115,800 A | 5/1992 | Matejevic et al. |
| 5,243,968 A | 9/1993 | Byun |
| 5,458,559 A | 10/1995 | Gauntlett |
| 6,183,414 B1 | 2/2001 | Wysor et al. |
| 6,248,059 B1 | 6/2001 | Gamper et al. |
| 6,277,062 B1 | 8/2001 | Vollrath et al. |
| 6,659,938 B1 | 12/2003 | Orlowski et al. |

FOREIGN PATENT DOCUMENTS

| DE | 4344686 | 6/1995 |
| EP | 510450 | 10/1992 |
| JP | 2000350741 | 12/2000 |
| JP | 2001299795 | 10/2001 |
| WO | WO97/26848 | 7/1997 |

OTHER PUBLICATIONS

Adam & Eve Brochure, Jul. 2002, p. 47.*
Xandria Collections Brochure, Feb. 2002, p. 29.*

* cited by examiner

*Primary Examiner*—John P Lacyk
(74) *Attorney, Agent, or Firm*—Polsinelli Shughart PC

(57) ABSTRACT

A vacuum device for facilitating the attainment of a penile erection is disclosed. The vacuum device comprises an inner tubular member slidably engaged with an outer tubular member with a sleeve member disposed inside the inner tubular member. The sleeve member defines a conduit having a plurality of nub-like protrusions adapted to maintain a sufficient degree of vacuum inside the device while simultaneously providing a massaging action.

30 Claims, 2 Drawing Sheets

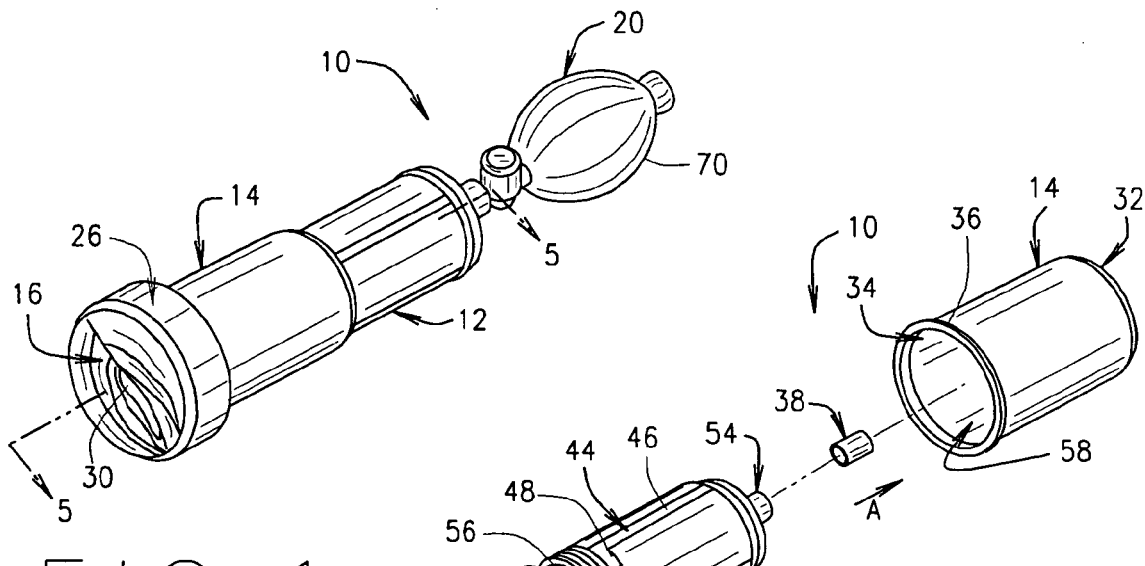
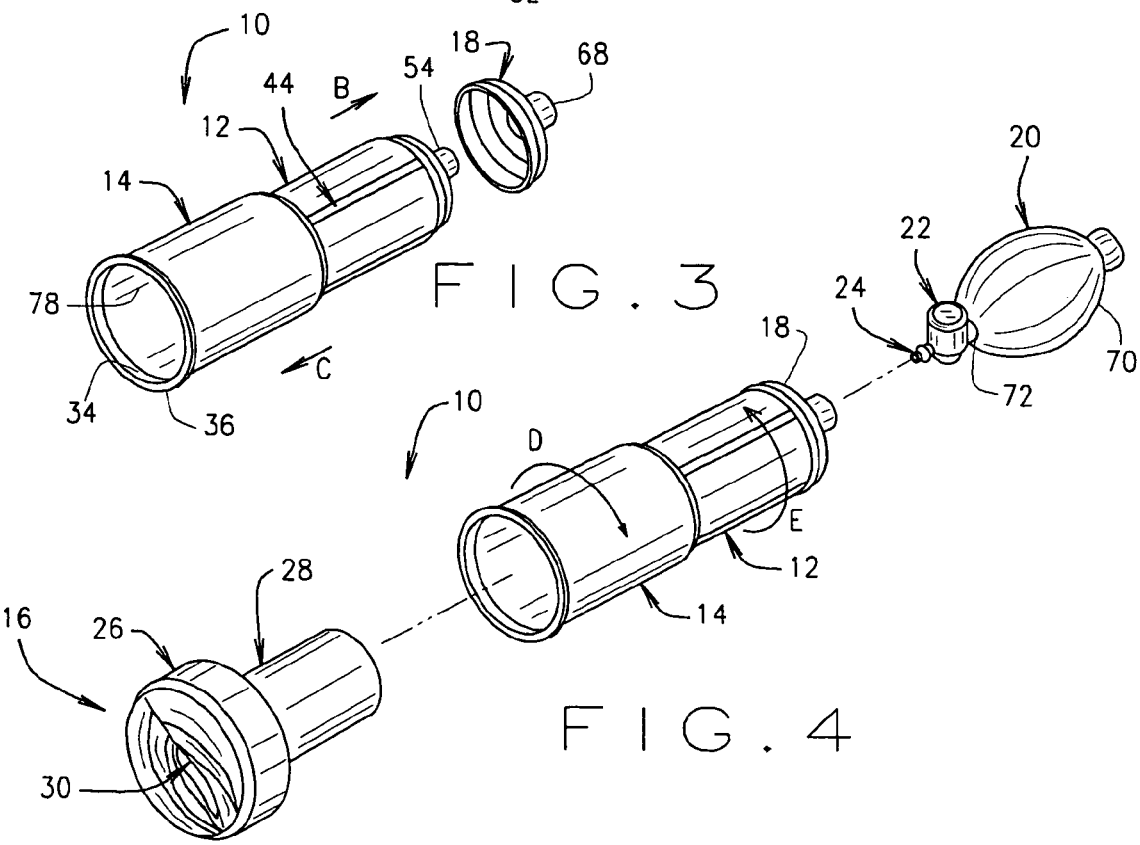

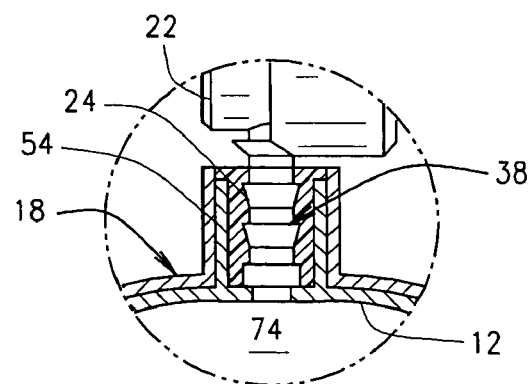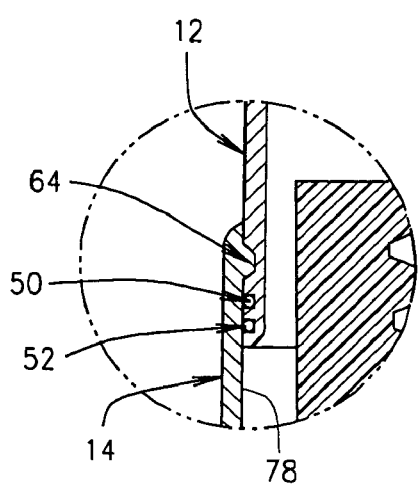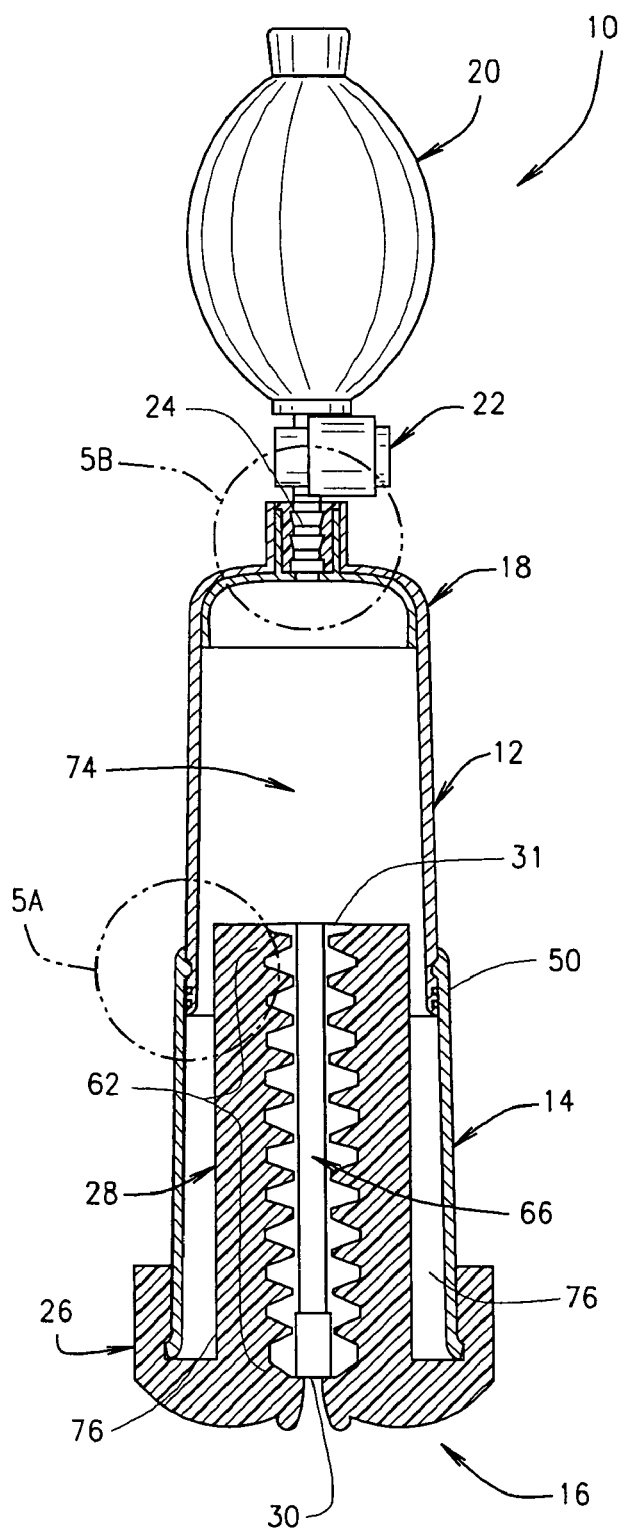
FIG. 5B
FIG. 5A
FIG. 5

COLLAPSIBLE VACUUM DEVICE

FIELD OF THE INVENTION

The present invention relates to an apparatus for assisting the user to attain a penile erection, and more particularly to a vacuum penile erection device.

BACKGROUND OF THE INVENTION

Vacuum penile erection devices for the treatment of impotence that assist the user in attaining a penile erection are well known in the art. Typically, such vacuum devices may comprise a hollow tubular member having an opening in communication with a cavity adapted to receive the penis. In addition, the tubular member may be in operative communication with a manual vacuum generating means, such as a flexible bulb or piston, for generating a vacuum inside the tubular member when the user repeatedly actuates the bulb or piston. A sleeve member may be disposed inside the tubular member that is adapted to engage the penis in order to maintain a sufficient level of vacuum between the penis and the tubular member during operation of the vacuum device. In addition, the sleeve member of the prior art may be configured as a smooth elastic sleeve member or ring made of a flexible material that the penis engages in order to maintain a sufficient vacuum inside the vacuum device during operation.

However, a sleeve member of the prior art adapted to engage the penis in such vacuum devices is designed to only maintain a sufficient degree of vacuum inside the device during operation and lack any means for simultaneously providing a massaging effect to the penis in order to facilitate the attainment of an erection by the user. Moreover, it may be desirable to provide a vacuum device that is easily disassembled for storage.

Therefore, there is a need in the art for a vacuum device that includes a removable sleeve member adapted to maintain a sufficient degree of vacuum when engaged with the penis, while also providing a massaging effect to the penis that facilitates the attainment of an erection by the user. There is a further need in the art for a vacuum device that is easily assembled and disassembled.

SUMMARY OF THE INVENTION

A primary object of the present invention is to provide a vacuum device that maintains a sufficient degree of vacuum inside the device while simultaneously providing a massaging effect to the penis in order to facilitate the attainment of an erection.

Another object of the present invention is to provide a vacuum device that is easily disassembled for storage.

A further object of the present invention is to provide a vacuum device having a disposable sleeve member that provides a massaging effect.

Another further object of the present invention is to provide a sleeve member for a vacuum device having an inner portion with a plurality of nub-like protrusions.

Yet another object of the present invention is to provide a vacuum device that may be quickly assembled and disassembled.

In a preferred embodiment, the present invention comprises a vacuum device comprising a body including an inner tubular member slidably engageable with an outer tubular member, and a sleeve member engageable within the outer tubular member, wherein the sleeve member includes an opening in communication with a conduit, the conduit defining a plurality of nub-like protrusions.

In another embodiment, the present invention comprises a sleeve member engageable with a vacuum device with the sleeve member comprising a sleeve body having a flange element and a tubular element, the flange element including an opening in communication with a conduit of the sleeve body defining a plurality of nub-like protrusions adapted to provide a massaging effect when a penis is disposed in said inner portion, while also maintaining a sufficient degree of vacuum inside the vacuum device.

In yet another embodiment, the present invention comprises a method of disassembling a vacuum device comprising:

a) providing a vacuum device comprising a body including an inner tubular member defining a chamber, the inner tubular member engaged to an outer tubular member, a sleeve member engaged within the outer tubular member, a cap member defining an aperture in communication with the chamber and engaged to one end of the inner tubular member, and a flexible bulb engaged to the cap member, the inner tubular member defining at least one slot engaged to a respective at least one protrusion defined by the outer tubular member;

b) rotating the inner tubular member relative to the outer tubular member such that at least one protrusion slidably engages a respective at least one slot; and c) pulling the inner tubular member away from the outer tubular member such that at least one protrusion disengages from said at least one slot.

In another embodiment, the present invention comprises a method of assembling a vacuum device comprising:

a) providing a vacuum device comprising a body including an inner tubular member defining a chamber, the inner tubular member engageable to an outer tubular member, a sleeve member engageable within the outer tubular member, a cap member defining an aperture in communication with the chamber and engageable to one end of the inner tubular member, and a flexible bulb engageable to the cap member, the inner tubular member defining at least one slot engageable to a respective at least one protrusion defined by the outer tubular member;

b) pushing the inner tubular member toward the outer tubular member such that the at least one protrusion is slidably engaged to a respective at least one slot; and c) rotating the inner tubular member relative to the outer tubular member such that the inner tubular member becomes fully engaged to the outer tubular member.

Additional objects, advantages and novel features of the invention will be set forth in the description which follows, and will become apparent to those skilled in the art upon examination of the following more detailed description and drawings in which like elements of the invention are similarly numbered throughout.

BRIEF DESCRIPTION OF THE DRAWINGS

FIG. 1 is a perspective view of the vacuum device according to the present invention;

FIGS. 2, 3 and 4 illustrate the sequence of assembling or disassembling the vacuum device according to the present invention;

FIG. 5 is a partial cross-sectional view of the vacuum device taken along line 5-5 of FIG. 1 according to the present invention;

FIG. 5A is an enlarged view of FIG. 5 of the vacuum device showing the engagement between the flexible bulb and cap member according to the present invention; and FIG. 5B is another enlarged view of FIG. 5 of the vacuum device showing the engagement between the inner and outer tubular members according to the present invention.

DETAILED DESCRIPTION OF THE INVENTION

Referring to the drawings, a vacuum device according to the present invention is illustrated and generally indicated as 10 in FIGS. 1-5. The vacuum device 10 comprises an inner tubular member 12 slidably engageable within an outer tubular member 14 adapted to be assembled in an operational configuration (FIG. 1) or quickly disassembled in a storage configuration (FIG. 5).

Referring to FIG. 2, the outer tubular member 14 defines a large bore 58 in communication with a proximal opening 32 and an opposing distal opening 34, while the inner tubular member 12 defines a small bore 60 in communication with a circular protrusion 54 at one end and a large opening 56 at another end. A sleeve 38 is adapted to be engaged within the circular protrusion 54. The vacuum device 10 further comprises a sleeve member 16 adapted to be disposed inside the large bore 58 through the large opening 56. The sleeve member 16 is adapted for maintaining sufficient vacuum inside the vacuum device 10 when the penis is inserted into the sleeve member 16 as well as provide a massaging effect to the penis as shall be discussed in greater detail below.

The outer tubular member 14 includes a flange 36 defined around the periphery of the distal opening 34. In addition, the outer tubular member 14 defines an inner surface 78 that includes a plurality of protrusions 64 (FIG. 5A) evenly positioned around the circumference of surface 78 which are adapted to engage the inner tubular member 12 during assembly of the vacuum device 10.

According to one aspect of the present invention, the inner tubular member 12 defines a pair of L-shaped slots 44 with each slot 44 including a horizontal slot 46 in communication with a vertical slot 48. Each L-shaped slot 44 is adapted to engage a respective protrusion 64 when engaging the inner tubular member 12 to the outer tubular member 14. Preferably, the angle defined between the horizontal slot 46 and vertical slot 48 is less than 90 degrees such that L-shaped slot 44 is more securely engageable with protrusion 64 when securing inner tubular member 12 with outer tubular member 14. In addition, the inner tubular member 12 defines first and second grooves 40 and 42 that are adapted to engage first and second sealing elements 50 and 52, respectfully, that provide a means for providing a fluid tight seal between the inner tubular member 12 and outer tubular member 14 when assembled. An end cap 18 defining a raised aperture 68 is engaged at one end of inner tubular member 12 during assembly for providing a site adapted to engage a flexible bulb 20 or other suitable means of generating a sufficient vacuum.

Referring to FIG. 4, flexible bulb 20 has a hollow body 70 that provides a means for generating a vacuum inside vacuum device 10 when repeatedly actuated by the user. In particular, the hollow body 70 defines an opening 72 engaged to a mechanical air valve 22 that permits selective fluid flow communication with the chamber 74 of inner tubular member 12 when engaged thereto. As shown in FIG. 5B, air valve 22 includes an air nozzle 24 adapted to engage the sleeve 38 disposed inside circular protrusion 54 of inner tubular member 12 for fluid flow communication with chamber 74.

Referring to FIG. 5, sleeve member 16 comprises a flange portion 26 and a tube portion 28. The flange portion 26 defines a first aperture 30 that communicates with a second aperture 31 through a conduit 66. Preferably, first aperture has the visual appearance of female gentilia. A circular slot 76 is defined between the flange portion 26 and tube portion 28 and is adapted to engage the outer tubular member 14 during assembly of the vacuum device 10. According to one aspect of the present invention, the conduit 66 defines a plurality of nub-like protrusions 62 adapted to surround and engage the penis when inserted into conduit 66 such that a seal is generated between the penis and the sleeve member 16 that maintains a sufficient degree of vacuum inside vacuum device 10 during operation. In addition, the nub-like protrusions 62 are made from a flexible, pliable material, such as rubber, that provides a massaging effect to the penis when a vacuum is generated inside the vacuum device 10. Preferably, the first aperture 30 has a realistic appearance of a female vagina and is made from a flexible, pliable material adapted to comfortably engage the user's penis.

Referring to FIG. 2, to assemble the vacuum device 10, the inner tubular member 12 with the first and second sealing elements 50 and 52 seated within respective first and second grooves 40 and 42 is inserted through large bore 58 of the outer tubular member 14 in direction A such that each slot 44 of inner tubular member 12 is aligned and engaged with a respective protrusion 64 of outer tubular member 14. As shown in FIG. 3, the protrusions 64 are then axially engaged along the horizontal slot 46 as the inner tubular member 12 is axially inserted through the large bore 58 in direction B and outer tubular member 14 in direction C.

Referring to FIG. 4, the user then rotates the outer tubular member 14 in direction D while rotating the inner tubular member 12 in counter direction E such that each protrusion 64 becomes engaged along a respective vertical slot 48. Once so engaged, the tube portion 28 of sleeve member 16 is inserted through the proximal opening 56 of outer tubular member 14 until the flange 36 abuts the bottom of slot 76. Preferably, the end cap 18 having an aperture 68 may be engaged to the inner tubular member 12 and the air valve 22 of flexible bulb 20 then engaged to circular protrusion 54 for establishing fluid flow communication with chamber 74.

Conversely, the user may disassemble the vacuum device 10 by rotating the inner tubular member 12 relative to the outer tubular member 14 in a manner opposite to directions D and E noted above such that each protrusion 64 slidably engages along vertical slot 48 until each protrusion 64 communicates with horizontal slot 46. The user then pulls the inner tubular member 12 away from the outer tubular member 14 in a manner opposite to direction B such that each protrusion 64 slidably engages along the horizontal slot 46 until disengaged from L-shaped slot 44. Once so disengaged, the user may then disengage the end cap 18 from the inner tubular member 12 and the sleeve member 16 disengaged from the outer tubular member 14 in order to disassemble the vacuum device 10. Preferably, the air valve 22 may also be disengaged from the inner tubular member 12.

In operation, the user inserts his penis through the first aperture 30 and into conduit 66 of sleeve member 16. The user then repeatedly actuates the flexible bulb 20 to generate a sufficient vacuum inside chamber 74 that applies a suction to the penis as vacuum is generated inside the vacuum device 10 while also providing a massaging effect to the penis from the engagement with the plurality of nub-like protrusions 62. This combination of suction and massaging action by vacuum device 10 provides a quick and effective means of permitting the user to attain and sustain a penile erection.

It should be understood from the foregoing that, while particular embodiments of the invention have been illustrated and described, various modifications can be made thereto without departing from the spirit and scope of the present invention is intended to be limited only by the appended claims.

What is claimed is:

1. A vacuum device comprising:
    a body including an inner tubular member capable of slidably engaging within an outer tubular member along a longitudinal axis of the outer tube, and
    a sleeve member engageable within said outer tubular member, wherein said sleeve member includes an opening in communication with a conduit, said conduit defining a plurality of protrusions.

2. The vacuum device according to claim 1, wherein said inner tubular member defines at least one slot and said outer tubular member defines at least one protrusion.

3. The vacuum device according to claim 2, wherein said at least one slot is adapted to engage said at least one protrusion.

4. The vacuum device according to claim 2, wherein said at least one slot comprises a vertical slot in communication with a horizontal slot.

5. The vacuum device according to claim 1, wherein said body defines a chamber.

6. The vacuum device according to claim 5, further comprising a flexible bulb in fluid flow communication with said chamber, said flexible bulb adapted to generate a vacuum inside said chamber.

7. The vacuum device according to claim 1, wherein said sleeve member further comprises a flange element and a tubular element.

8. The vacuum device according to claim 1, wherein said inner tubular member defines a circular protrusion.

9. The vacuum device according to claim 8, further comprising an end cap adapted to engage said inner tubular member, said end cap defining an aperture engaged to said circular protrusion.

10. The vacuum device according to claim 1, wherein said opening of said sleeve has the visual appearance of female genitalia.

11. The vacuum device according to claim 4, wherein said vertical slot and said horizontal slot define an angle of less than 90 degrees.

12. A sleeve member engageable with a vacuum device comprising:
    a sleeve body having a flange element and a tubular element, said flange element being adapted to engage and seal an opening of the vacuum device, said opening further defining an interior perimeter and an exterior perimeter of the vacuum device, such that said flange element radially extends beyond the opening and engages the vacuum device along the exterior perimeter, and said flange element including an opening in communication with the tubular element; said tubular element defining a conduit with said conduit further defining a plurality of protrusions.

13. The sleeve member according to claim 12, wherein said protrusions are adapted to provide a massaging effect when a penis is disposed in said inner portion while also maintaining a sufficient degree of vacuum inside the vacuum device.

14. A method disassembling a vacuum device comprising:
    a) providing a vacuum device comprising a body including an inner tubular member defining a chamber, said inner tubular member engageable to an outer tubular member, a sleeve member engageable within said outer tubular member, a cap member defining an aperture in communication with said chamber and engageable to one end of said inner tubular member, and a flexible bulb engageable to said cap member, said inner tubular member defining at least one slot engageable to a respective at least one protrusion defined by said outer tubular member;
    b) rotating said inner tubular member relative to said outer tubular member such that at least one protrusion slidably engages a respective at least one slot; and
    c) pushing said inner tubular member along a longitudinal axis of said outer tubular member so that said inner tubular member is passed through said outer tubular member;
    d) pulling said inner tubular member away from said outer tubular member such that said at least one protrusion disengages from said at least one slot.

15. The method according to claim 14, wherein said method further includes the step of disengaging said flexible bulb from said cap member.

16. The method according to claim 14, wherein said method further includes the step of disengaging said sleeve member from said outer tubular member.

17. The method according to claim 14, wherein said method further includes the step of disengaging said cap member from said inner tubular member.

18. The method according to claim 14, wherein said at least one slot is L-shaped.

19. The method according to claim 14, wherein said at least one slot comprises a vertical slot in communication with a horizontal slot.

20. The method according to claim 19, wherein said step of rotating includes slidably engaging said at least one protrusion with said vertical slot.

21. The method according to claim 19, wherein said step of pulling includes slidably disengaging said at least one protrusion from said horizontal slot.

22. The method according to claim 19, wherein said vertical slot and said horizontal slot define an angle of less than 90 degrees.

23. A method of assembling a vacuum device comprising:
    a) providing a vacuum device comprising a body including an inner tubular member defining a chamber, said inner tubular member engageable to an outer tubular member, a sleeve member engageable within said outer tubular member, a cap member defining an aperture in communication with said chamber and engageable to one end of said inner tubular member, and a flexible bulb engageable to said cap member, said inner tubular member defining at least one slot engageable to a respective at least one protrusion defined by said outer tubular member;
    b) pushing said inner tubular member along a longitudinal axis of said outer tubular member such that said inner tubular member is passed through said outer tubular member and said at least one protrusion is slidably engaged to a respective said at least one slot;
    c) pulling said inner tubular member away from said outer tubular member such that said at least one protrusion remains engaged to said at least one slot; and
    d) rotating said inner tubular member relative to said outer tubular member such that said inner tubular member becomes fully engaged to said outer tubular member.

24. The method according to claim 23, wherein said method further includes the step of engaging said sleeve member within said outer tubular member.

25. The method according to claim 23, wherein said method further includes the step of engaging said cap member to said inner tubular member.

26. The method according to claim 23, wherein said at least one slot is L-shaped.

27. The method according to claim 23, wherein said at least one slot comprises a vertical slot in communication with a horizontal slot.

28. The method according to claim 27, wherein said step of rotating includes slidably engaging said at least one protrusion with said vertical slot.

29. The method according to claim 27, wherein said step of pushing includes slidably engaging said at least one protrusion to said horizontal slot.

30. The method according to claim 27, wherein said vertical slot and said horizontal slot define an angle less than 90 degrees.

* * * * *